United States Patent
Collin et al.

(10) Patent No.: US 9,625,817 B2
(45) Date of Patent: Apr. 18, 2017

(54) PHOTORESIST WITH POSITIVE-RESIST BEHAVIOUR, METHOD FOR PHOTOCHEMICAL STRUCTURING THEREOF, METHOD FOR THE PRODUCTION OF SILANES AND OF SILICIC ACID (HETERO)POLY(CO)CONDENSATES WITH POSITIVE-RESIST BEHAVIOUR AND ALSO SILICIC ACID (HETERO)POLY(CO)CONDENSATES

(71) Applicant: FRAUNHOFER-GESELLSCHAFT ZUR FÖRDERUNG DER ANGEWANDTEN FORSCHUNG E.V., München (DE)

(72) Inventors: Daniela Collin, Werneck (DE); Gerhard Domann, Höchberg (DE)

(73) Assignee: FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

(21) Appl. No.: 14/767,347

(22) PCT Filed: Feb. 25, 2014

(86) PCT No.: PCT/EP2014/053580
§ 371 (c)(1),
(2) Date: Aug. 12, 2015

(87) PCT Pub. No.: WO2014/128303
PCT Pub. Date: Aug. 28, 2014

(65) Prior Publication Data
US 2015/0370169 A1  Dec. 24, 2015

(30) Foreign Application Priority Data
Feb. 25, 2013 (DE) .......... 10 2013 003 329

(51) Int. Cl.
| | | |
|---|---|---|
| G03F 7/075 | (2006.01) | |
| G03F 7/039 | (2006.01) | |
| G03F 7/004 | (2006.01) | |
| G03F 7/20 | (2006.01) | |
| G03F 7/38 | (2006.01) | |
| G03F 7/32 | (2006.01) | |
| G03F 7/16 | (2006.01) | |
| C07F 7/18 | (2006.01) | |
| C08G 77/28 | (2006.01) | |
| C08G 77/48 | (2006.01) | |

(52) U.S. Cl.
CPC .......... *G03F 7/0757* (2013.01); *C07F 7/1804* (2013.01); *C07F 7/1836* (2013.01); *C08G 77/28* (2013.01); *C08G 77/48* (2013.01); *G03F 7/0045* (2013.01); *G03F 7/039* (2013.01); *G03F 7/0392* (2013.01); *G03F 7/16* (2013.01); *G03F 7/168* (2013.01); *G03F 7/20* (2013.01); *G03F 7/322* (2013.01); *G03F 7/38* (2013.01)

(58) Field of Classification Search
None
See application file for complete search history.

(56) References Cited

U.S. PATENT DOCUMENTS

| | | | |
|---|---|---|---|
| 4,665,006 A | 5/1987 | Sachdev et al. | |
| 5,612,170 A | 3/1997 | Takemura et al. | |
| 5,779,993 A * | 7/1998 | Gentry ................. | B01D 3/007 261/114.1 |
| 2003/0064320 A1* | 4/2003 | Hanabata .............. | G03F 7/0382 430/270.1 |
| 2004/0161698 A1 | 8/2004 | Kanagasabapathy et al. | |
| 2005/0009982 A1 | 1/2005 | Inagaki et al. | |
| 2005/0042542 A1 | 2/2005 | Foster et al. | |
| 2005/0079443 A1 | 4/2005 | Noda et al. | |

(Continued)

FOREIGN PATENT DOCUMENTS

| | | |
|---|---|---|
| EP | 0 410 606 A2 | 1/1991 |
| EP | 0 586 476 A1 | 3/1994 |

(Continued)

OTHER PUBLICATIONS

An excerpt obtained from the internet website https://en.wikipedia.org/wiki/Thiol-ene_reaction (date unknown).*
European Patent Office, International Search Report in International Application Mo. PCT/EP2014/053580 (Jun. 4, 2014).
European Patent Office, Written Opinion in International Application Mo. PCT/EP2014/053580 (Jun. 4, 2014).

(Continued)

*Primary Examiner* — Sin Lee
(74) *Attorney, Agent, or Firm* — Leydig, Voit & Mayer, Ltd.

(57) ABSTRACT

The present invention relates to a special heteropolymer, namely a silicic acid (hetero)poly(co)condensate with positive-resist behavior which is distinguished by polycondensation or copolycondensation of specially modified silanes. The invention relates likewise to monomeric silanes from which the corresponding heteropolymers, i.e. the silicic acid (hetero)poly(co)condensates, can be produced. The silicic acid (hetero)poly(co)condensates according to the invention can be used for a photoresist which has positive-resist behavior. In addition, the invention relates to corresponding methods both for the production of the silanes, the silicic acid (hetero)poly(co)condensates or a method for photochemical structuring of the photoresist according to the invention which is based on the silicic acid (hetero)poly(co) condensates.

11 Claims, 1 Drawing Sheet

(56) References Cited

U.S. PATENT DOCUMENTS

| | | | |
|---|---|---|---|
| 2007/0065753 A1 | 3/2007 | Mizutani et al. | |
| 2007/0148586 A1 | 6/2007 | Uh et al. | |
| 2008/0188581 A1* | 8/2008 | Lee | B82Y 30/00 |
| | | | 521/154 |
| 2009/0068586 A1 | 3/2009 | Nakamura et al. | |
| 2009/0252471 A1 | 10/2009 | Kondo et al. | |
| 2011/0008589 A1 | 1/2011 | Kimura et al. | |
| 2011/0065050 A1 | 3/2011 | Li et al. | |
| 2011/0300596 A1* | 12/2011 | Lee | C07C 29/149 |
| | | | 435/160 |
| 2013/0101942 A1* | 4/2013 | Tanaka | G03F 7/11 |
| | | | 430/325 |

FOREIGN PATENT DOCUMENTS

| | | |
|---|---|---|
| EP | 1 265 103 A1 | 12/2002 |
| JP | H04-050947 A | 2/1992 |
| JP | H05-323611 A | 12/1993 |
| KR | 2009-0104649 A | 10/2009 |
| WO | WO 92/21326 A1 | 12/1992 |
| WO | WO 94/11788 A1 | 5/1994 |

OTHER PUBLICATIONS

International Bureau of WIOP, International Preliminary Report on Patentability in International Application Mo. PCT/EP2014/053580 (Sep. 3, 2015).

Gabor et al., "Block and random copolymer resists designed for 193-nm lithography and environmentally friendly supercritical CO2 development," *Proc. SPIE 2724, Advances in Resist Technology and Processing XIII*, pp. 410-417 (1996).

Gallagher-Wetmore et al., "Supercritical fluid processing: a new dry technique for photoresist developing," *Proc. SPIE vol. 2438, Advances in Resist Technology and Processing XII*, 694 (Jun. 9, 1995).

Haas et al., "Functionalized coating materials based on inorganic-organic polymers," *Thin Solid Films*, vol. 351, Issues 1-2, pp. 198-203 (1999).

Haas, "Hybrid Inorganic—Organic Polymers Based on Organically Modified Si-Alkoxides," *Adv. Eng. Mater.*, 2(9): 571-582 (2000).

Hatakeyama et al., "Discrimination enchancement in polysilsesquioxane-based positive resists for ArF lithography," *Proc. SPIE. vol. 3333, Advances in Resist Technology and Processing XV*, 62. (Jun. 29, 1998).

Noguchi et al., "A Novel Silicon-Containing Resist for Half-Micron Photolithography," *Polym. Microelectron Proc. Int. Symp.*, pp. 305-316 (1990).

Popall et al., "A new inorganic-organic polymer for the passivation of thin film capacitors," *Journal of Sol-Gel Science and Technology*, vol. 2, No. 1, pp. 157-160 (1994).

Sanchez et al., "Applications of hybrid organic—inorganic nanocomposites," *J. Mater. Chem.* 15, pp. 3559-3592 (2005).

Tanaka, "Silicon-Based Photoresist" *Radiation Curing in Polymer Science and Technology, vol. IV, Practical Aspects and Applications*, JP Fouassier and JF Rabek, Editors, Elsevier Applied Science, NY, pp. 361-386 (1993).

* cited by examiner

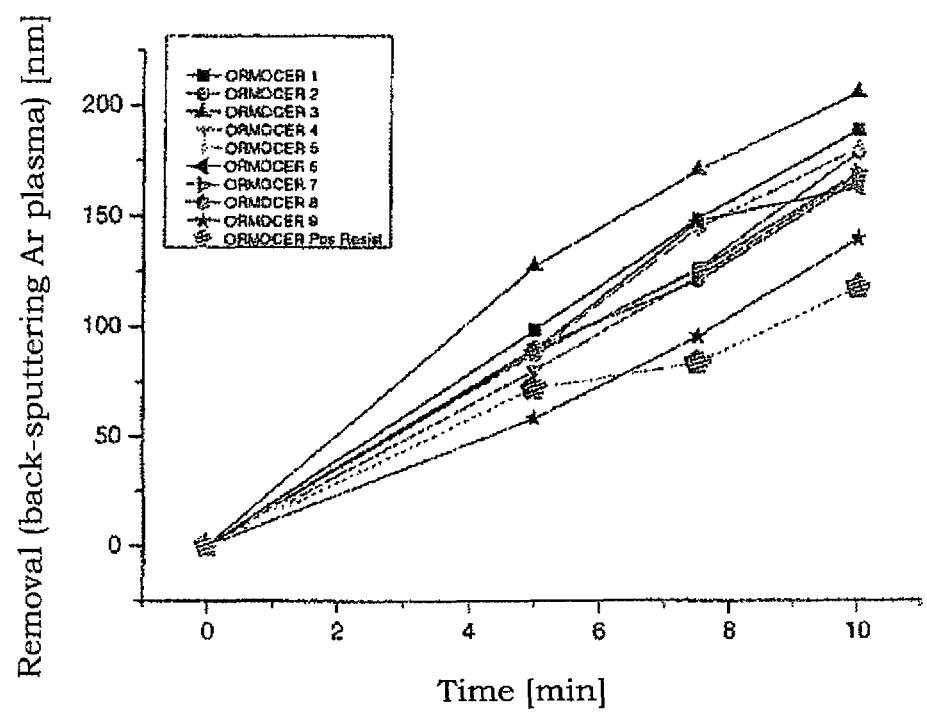

PHOTORESIST WITH POSITIVE-RESIST BEHAVIOUR, METHOD FOR PHOTOCHEMICAL STRUCTURING THEREOF, METHOD FOR THE PRODUCTION OF SILANES AND OF SILICIC ACID (HETERO)POLY(CO)CONDENSATES WITH POSITIVE-RESIST BEHAVIOUR AND ALSO SILICIC ACID (HETERO)POLY(CO)CONDENSATES

CROSS-REFERENCE TO RELATED APPLICATIONS

This patent application is the U.S. national phase of International Application No. PCT/EP2014/053580, filed on Feb. 25, 2014, which claims the benefit of German Patent Application No. 10 2013 003 329.2, filed Feb. 25, 2013, the disclosures of which are incorporated herein by reference in their entireties for all purposes.

The present invention relates to a photoresist which comprises a special heteropolymer, namely a silicic acid (hetero)poly(co)condensate with positive-resist behaviour which can be produced by polycondensation or copolycondensation of specially modified silanes. The invention relates likewise to monomeric silanes from which the corresponding heteropolymers, i.e. the silicic acid (hetero)poly(co)condensates, can be produced. The silicic acid (hetero)poly(co)condensates according to the invention can be used for a photoresist which has a positive-resist behaviour. In addition, the invention relates to corresponding methods both for the production of silanes, the silicic acid (hetero)poly(co)condensates or a method for photochemical structuring of the photoresist according to the invention which is based on the silicic acid (hetero)poly(co)condensates.

Photoresists or even photosensitive coatings are frequently used today in UV-lithographic production of integrated circuits. A distinction is thereby made between positive-tone resists, in which the solubility is increased by interaction with light, and negative-tone resists, in which the solubility is reduced. The increase in solubility is frequently achieved by the production of functional groups or by bond breakages and hence reduction in the molecular weight. In the case of reduction in solubility in contrast, products with a greater molecular weight than the initial material are generated by polymerisation reactions, which products can then no longer be dissolved in the solvent. Photoresists with positive-tone behaviour generally have better resolution than negative-tone resists because, in the case of the latter, chain reactions frequently underlie the crosslinkage reaction and—in contrast to the individually induced bond breakages of the positive-tone resists—have a greater reaction volume. In order to enable a positive behaviour, increased solubility must be generated. This can be effected, on the one hand, by bond breakages in the polymer chain, i.e. reduction in molecular mass or else by chemical reactions which result in the production of different functional groups and hence lead to altered polarity. For solubility in aqueous solvents, polar groups, such as for example alcohol- or carboxylic acid groups, but basically also amino functions, are suitable. The reaction with respect to these functional groups can be effected intrinsically or else by additional additives or initiators.

When used as sacrificial resists, the structured photoresist layer, for its part, is used as mask for the deposition of inorganic layers or for etching the materials exposed between the structures. Most widespread is thereby etchstructuring. As a result, a second requirement is made of the photoresist. This must remain stable under the etching conditions, such as e.g. $O_2$ plasma, and likewise must not be removed.

The etching stability of purely organic photoresists can be improved by the use of inorganic components, in part because, in the case of using silicon-organic components, a surface film which is stable for the etching conditions is formed by the interaction of the plasma with silicon-organic films with $SiO_2$ formation. Based thereon, some publications already report the incorporation of silicon-containing compounds in positive-photoresists. The silicon-containing positive-photoresists resulting therefrom are based in part on two-component systems: one component consists of a silicon-containing polymer which is soluble in the aqueous developer, the other component consists of a polymer which is insoluble in aqueous solvents, such as for example DNQ, which reacts with interaction with actinic radiation and forms polar groups, as a result of which, after exposure, also the second component and hence the entire photoresist becomes soluble in the aqueous developer [Y. Kimura, T. Etou, M. Kondo, US 20110008589A1; T. Aoai, K. Mitzutani, EP 410606 A2; A. Tanaka, Radiat. Curin Polym. Sci. Technol. 19934381-386; D. S. Uh, C. I. Oh, D. H. Kim, H. C. Yun, J. K. Lee, I. Nam, J. S. Kim, US 20070148586 A; K. Mizutani, H. Kanda, H. Inabe, US 20070065753 A1]. In further works, these two components, i.e. silicon-containing monomers and also purely organic monomers which have the photolabile groups, are crosslinked by covalent bonds and form (block)copolymers [A. H. Gabor, R. D. Allen, P. Gallagher-Wetmore, C. K. Ober, Proc. SPIEE—the International Society for Optical Engineering, 1996, 2724, 410-417; E. W. Van der Drift, J. C. Van de Grampel, R. Puyenbroek, B. Rousseeuw, WO 9411788 A1; K. G. Sachdev, R. W. Kwong, M. M. Khojasteh, H. S. Sachdev, U.S. Pat. No. 4,665,006 A; P. Foster, G. Spaziano, B. B. De, US 20050042542 A1]. In addition, the silicon-containing components can also be implemented after formation of the network of the photolabile components as so-called macromers, by substitution in the side chains of the network. All these methods have the basic disadvantage that, due to the silicon-free components, the positive etching properties of the silicon are attenuated.

Other works report about the introduction of the photolabile group, e.g. as ester, in the side chains of the network constructed purely from silicon-containing monomers. Examples of this are ladder-forming networks, so-called polysilsesquioxanes, which have photolabile groups in cyclohexyl side chains [J. Hatakeyama, M. Nakashima, I. Kaneko, S. Nagura, T. Ishihara, Proc. SPIEE—the International Society for Optical Engineering, 1998333362-72].

The introduction of these protective groups is frequently effected by the reaction of hydroxyl groups of the silsesquioxane side chains with α-halogen carboxylic acid esters [T. Nakamuura, K. Tamura, T. Yamada, T. Hirayama, D. Kawana, T. Hosono, US20090068586 A1]. In addition, substituents with photolabile groups can be effected by hydrosilylation reactions, i.e. the catalysed reaction of a C=C bond of the future substituent with Si—H groups of the silane or by substitution of hydroxyl groups of polycyclic side chains (e.g. norbornenes) [K. Noda, K. Takemura, Y. Hamada, M. Nakashima, US 20050079443 A1]. In addition to ester groups, also substituents can be bonded to the alkoxysilane, which substituents have the DNQ group mentioned already above and therefore are intrinsically photolabile [T. Noguchi, K. Nito, H. Tomita, J. Seto, Polym. Microelectron. Proc. Int. Symp. 1990305-316].

In further works, the light-induced reaction of polysilanes to form polysiloxanes for structuring with positive-behaviour is used since the reaction product is soluble in aqueous solvents [P. Gallagher-Wetmore, G. M. Wallraff, R. D. Allen, Proc. SPIEE—the International Society for Optical Engineering, 19952438694-708]. Photoresists which are highly hydrolysis-sensitive, such as e.g. silazanes, can be hydrolysed and degraded under the effect of light with the protons formed by the catalyst and also the moisture from the environment [W. Li, G. S. Sandu, US 20110065050 A1]. The resulting, ceramic-like layer is soluble in aqueous solvents and can be removed. Since this layer can however likewise be insulating and stable relative to the plasma used in the etching step, an exposure step once again for forming a structured ceramic-like $SiO_2$ layer follows after development with this structuring method. A further possibility for introducing photolabile groups is offered by sulphonamides [S. Kanagasabapathy, G. G. Barclay, US 20040161698 A1].

The water solubility of the photoresist can be further increased by further substituents, such as e.g. fluorides [K. Noda, K. Takemura, Y. Hamada, M. Nakashima, US 20050079443 A1]. However, the incorporation of these substituents is not possible in an infinitely high proportion since the etching properties are consequently reduced. Introduction of these substituents is likewise basically possible for the present invention, e.g. by combined hydrolysis and condensation of the alkoxysilane which carries the photolabile group, and of a fluorinated alkoxysilane.

Furthermore, it is possible to increase the resolution of the ORMOCER®-containing photoresist, presented here, with positive-tone behaviour by an additional additive being added, which additive traps the reactive species which lead to the light-induced reaction and consequently prevents the reactive species from diffusing in large numbers into the unexposed regions and likewise being able to induce the formation of soluble components there. Amines, as were also reported in numerous other works relating to photoresists with positive-tone behaviour are for example also suitable for this purpose.

ORMOCER®s are based on hydrolysed and condensed alkoxysilanes or alkoxy element compounds, such as e.g. Ti, Zr. In the case of systems made purely of alkoxysilanes, functional groups can be integrated in the material by means of the stable Si—C bond, which groups are also contained still in the resulting material after hydrolysis and condensation of the silane (mono-, di- or trialkoxysilane). The transition metals, such as e.g. Zr or Ti, form, in contrast, hydrolysis-sensitive bonds to carbon substituents. The integration of functional groups must hereby be effected therefore via stable chelate complexes since only the thereby formed metal-ligand bonds are hydrolysis-stable.

The ORMOCER®s form a material class which, because of the versatility of the functional groups which can be integrated in the alkoxysilanes, can have properties of ceramic materials, silicones, organic polymers or even glasses [K.-H. Haas, Adv. Engin. Mater. 20002(9), 571-582]. As a result of the large number of combination possibilities, the mechanical, electrical, thermal and optical properties of thin ORMOCER® layers can be varied within a wide range. Examples of functional ORMOCER® layers are waveguide materials [N. Kondo, T. Hayashi, M. Popall, L. Frohlich, R. Houbertz, S. Cochet, US 20090252471 A1], scratch-proof coatings [K.-H. Haas, S. Amberg-Schwab, K. Rose, Thin Solid Films, 1999351, 198-203], passivation layers for optical and electronic components [M. Popall, J. Kappel, M. Pilz, J. Schulz, J. Sol-Gel Sci. Technol. 19942, 157-160], surface coating of soft, flexible polymer substrates and films [C. Sanchez, B. Man, P. Belleville, M. Popall, J. Mater. Chem. 2005, 15 (35-36)3559] or of temperature-sensitive substrates [K.-H. Haas, Adv. Engin. Mater. 20002(9), 571-582] and also dirt-repellent, anti-adhesive or antistatic coatings [K.-H. Haas, S. Amberg-Schwab, K. Rose, Thin Solid Films, 1999351, 198-203].

Starting herefrom, it was the object of the present invention to produce the previously presented hybrid polymer materials (Ormocers or silicic acid (hetero)poly(co)condensates, in which the previously mentioned good properties of the Ormocers are supplemented by a positive-tone character. In addition, it is the object of the present invention to indicate corresponding monomeric materials from which the corresponding Ormocer polymers can be produced or to demonstrate purposes of use of such polymer systems. Furthermore, it is the object of the present invention to demonstrate production possibilities for the previously mentioned substance classes.

These objects are achieved by a photoresist which comprises a silicic acid (hetero)poly(co)condensate having the features of patent claim 1, a method for photochemical structuring of the photoresist according to the invention having the features of patent claim 4, a method for the production of a silane with a positive-resist method having the features of patent claim 7, a method for the production of a silicic acid (hetero)poly(co)condensate having the features of patent claim 9 and also a silicic acid (hetero)poly (co)condensate with positive-resist behaviour having the features of patent claim 12. The respective dependent patent claims thereby represent advantageous developments.

According to a first aspect of the present invention, a method for the production of silanes with positive-resist behaviour according to general formula I

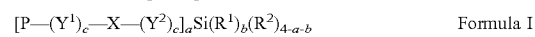

Formula I is hence described,

P representing a group which can be made photolabile or is photolabile,

X a functional crosslinkage produced by a chemical reaction, $Y^1$ and $Y^2$ being the same or different with each occurrence and being selected from the group consisting of saturated or unsaturated alkylene groups with 1 to 18 carbon atoms, cycloaliphatic groups with 6 to 24 carbon atoms or aromatic groups with 6 to 24 carbon atoms, $R^1$ being selected from the group consisting of linear or branched alkyl radicals with 1 to 18 carbon atoms, cycloaliphatic groups with 6 to 24 carbon atoms or aromatic groups with 6 to 24 carbon atoms, $R^2$ representing an —$OR^3$ group, $R^3$ being selected from the group consisting of linear or branched alkyl radicals with 1 to 18 carbon atoms, cycloaliphatic groups with 6 to 24 carbon atoms or aromatic groups with 6 to 24 carbon atoms, a being 1, 2 or 3 b being 0, 1 or 2, with the condition that a and b are chosen such that there applies: 4-a-b≥1 c being the same or different with each occurrence and being 0 or 1, in which a compound of general formula II

Formula II is converted with a compound of general formula III

Formula III to form the compound of general formula I, in the compounds of general formulae II and III the radicals P, $Y_1$, $Y^2$, $R^1$, $R^2$, a, b and c having the above-indicated meaning and $X^1$ and $X^2$ being functional groups which react to form the functional crosslinkage X.

The silane according to general formula I, which is produced according to the invention, thereby has a group which can be made photolabile or is photolabile. There are thereby understood by a group which can be made photolabile, functional groupings which can be split or modified indirectly by photochemical induction. An auxiliary reagent is necessary for this purpose, which reagent degrades during irradiation and thereby releases an active species which splits or modifies the group which can be made photolabile. A photolabile grouping is directly light-sensitive so that direct modification or splitting of this photolabile group is effected during light irradiation. Preferably, these groupings have light sensitivity in the visible range of the spectrum, however likewise a UV sensitivity or infrared sensitivity can be provided. The group P can thereby be chosen according to the desired purpose of use and be coordinated to the corresponding requirements.

The grouping $R^2$ thereby represents an oxo grouping, for example an alkoxy group, in particular an ethoxy- or methoxy group. The group $R^2$ is hence hydrolysis-sensitive so that the corresponding silane according to formula I can be crosslinked by polycondensation or copolycondensation under corresponding conditions.

The indices a and b can thereby be chosen freely according to the indicated conditions, a preferred embodiment, given by way of example, provides: b=0, a=1.

The present invention hence offers an extension of the reaction paths which are possible for the introduction of the photolabile group. The ester is hereby a bonded Michael-type reaction of a thiol group with a C=C bond to the underlying alkoxysilane. Basically suitable as substituents with photolabile groups are therefore double bond-containing carboxylic acid esters, in the case of which the C=C groups are bonded on the carboxylate side. Particularly preferred thereby are (meth)acrylic acid esters which are activated by the conjugation of C=C— and C=O bonding, particularly for the addition of a thiol. The alkoxy group of the photolabile ester should typically form the basis of a tertiary alcohol in order to increase the chemical affinity to the acid-catalysed hydrolysis, i.e. deprotection by the photoacid generated by means of actinic radiation.

The compound according to general formula I is produced by conversion of the compounds of general formula II with compounds of general formula III.

The groupings $X^1$ and $X^2$ are thereby functional groups which react to form the functional crosslinkage X.

The present invention hence offers an extension of the reaction paths which are possible for the introduction of the photolabile group. The ester is hereby bonded by a Michael-type reaction of a thiol group with a C=C bond to the underlying alkoxysilane. Basically suitable as substituents with photolabile groups are therefore double bond-containing carboxylic acid esters, in the case of which the C=C groups are bonded on the carboxylate side. Particularly preferred thereby are (meth)acrylic acid esters which are activated by the conjugation of C=C— and C=O bonding, particularly for the addition of a thiol. The alkoxy group of the photolabile ester should typically form the basis of a tertiary alcohol in order to increase the chemical affinity to the acid-catalysed hydrolysis, i.e. deprotection by the photoacid generated by means of actinic radiation.

The stoichiometric ratio of the compounds of general formulae II and III thereby depends of course upon the type of groupings $X^1$ and $X^2$ which are used, preferably groupings $X^1$ and $X^2$ are chosen for the production of the crosslinkage X which allow as equimolar a ratio of the compounds of formulae II and III as possible so that high economy of the reaction is provided.

Preferred groups P which can be made photolabile are thereby selected from the group consisting of radicals of general formula IV

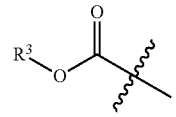

$R^3$ being selected from the group consisting of linear or branched alkyl radicals with 1 to 18 carbon atoms, preferably tertiary alkyl groups, such as e.g. t-butyl-, 1-ethylnorbornyl-, 1-methylcyclohexyl-, 1-ethylcyclopentyl-, 2(2-ethyl)adamantyl- or t-amyl groups; trialkylsilyl groups, such as e.g. trimethylsilyl-, triethylsilyl- or dimethyl-tert-butylsilyl groups; ester groups, such as e.g. t-butoxycarbonyloxy (t-BOC) or oxoalkyl groups (e.g. 3-oxocyclohexyl group).

Groups of this type are distinguished by being able to be modified by a corresponding reagent which is produced during irradiation. In the case of the example of the grouping according to the above-indicated formula IV, the modification is effected by saponification of the ester so that, from a relatively hydrophobic radical, a relatively hydrophilic grouping, for example the free carboxylic acid, can be produced, accompanied by a significant change in polarity of the silane. In the case where the silane is polymer-bonded, e.g. in an Ormocer network (as is described further on in more detail), the change in polarity is of course also valid for the produced polycondensates or copolycondensates.

The previously mentioned preferred radicals $R^3$ altogether represent excellent starting groups so that simple and comprehensive saponification of the ester group is possible.

Preferred photolabile groups which can be modified directly chemically by irradiation are thereby selected in particular from the group consisting of groupings which can be disassociated by means of photoirradiation. Such photolabile groups are mentioned for example in EP 0 586 476 A2, with respect to possible usable photolabile groups for the present invention, reference is made in particular also to this publication in this regard. All of the photolabile groups mentioned there can also be used according to the present invention. A particularly preferred photolabile group is thereby the 1,2-diazonaphthoquinone grouping.

A preferred functional crosslinkage X is thereby selected from one of the subsequently illustrated groupings:

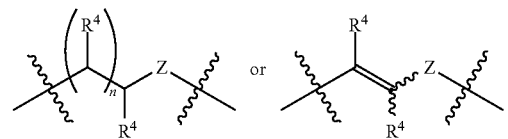

Z being selected from the group consisting of S, O, $NR^4$, $C(R^4)_2$, $R^4$ being the same or different with each occurrence and being selected from the group consisting of hydrogen and also linear or branched alkyl radicals with 1 to 18 carbon atoms, cycloaliphatic groups with 6 to 24 carbon atoms or aromatic groups with 6 to 24 carbon atoms and n being 0 or 1.

The grouping X illustrated on the left at the top can be produced for example by addition reaction whilst the grouping X illustrated on the right is accessible for example by cross-couplings etc.

Hence, the groups $X^1$ and $X^2$ contained in the above-indicated formulae III are preferably groups which react with each other by means of addition, substitution, cross-coupling or metathesis to form the functional crosslinkage X.

Subsequently, particularly preferred pairings of groupings $X^1$ and $X^2$ which can be used according to the present invention in order to obtain the functional crosslinkage X are illustrated. In a first variant, $X^1$ represents the subsequently illustrated grouping

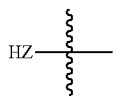

and $X^2$ is selected from the subsequently illustrated groupings.

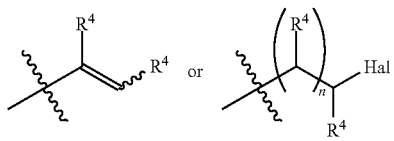

Hal hereby means Cl, Br or I.

The variables contained in the previously mentioned formulae thereby correspond to the definitions indicated already further back. This detail also applies for all of the subsequently mentioned formulae and also the contained variables, these are not mentioned in more detail in order to avoid repetition and for reasons of clarity but correspond respectively to the definitions indicated further back.

According to the previously mentioned pairing of groupings $X^1$ and $X^2$, the functional crosslinkage X can be prepared in particular by addition of the grouping HZ— to a double bond or by nucleophilic substitution of the corresponding grouping HZ— to an alkyl halide.

Alternatively and likewise preferably, the polarity of the two groupings $X^1$ and $X^2$ can however be reversed. According to this variant, it is preferred if $X^1$ is selected from the subsequently illustrated groupings

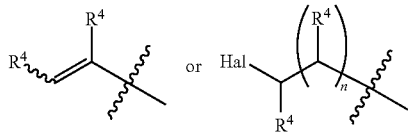

and $X^2$ represents the subsequently illustrated grouping

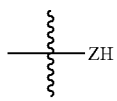

Hal meaning Cl, Br or I.

In a particularly preferred variant, the silane of general formula I has the following structural formula

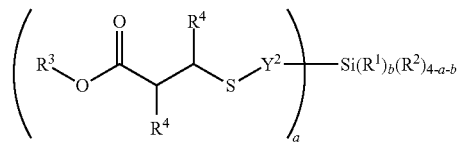

the corresponding silane is thereby producible by reaction of compounds of general formula II with the subsequent structure

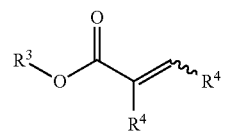

and a compound of general formula III with the subsequent structure

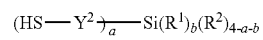

The silane of general formula I is obtained by thiol-ene addition of the compound of general formula II and the compound of general formula III.

In addition, the invention relates to a method product of the previously presented method according to the invention, i.e. a silane with positive-resist behaviour according to general formula I

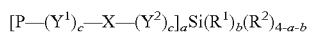   Formula 1

All of the parameters used (i.e. the variables indicated in formula I) or preferred embodiments with respect to the variables correspond thereby in fact to the previously presented embodiments.

In particular and particularly preferably, the silane according to the invention has the subsequent structure

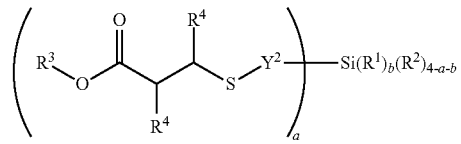

According to a further aspect, the present invention relates to a method for the production of a silicic acid (hetero)poly(co)condensate with positive-resist behaviour from a silane of general formula I, as defined above, in which a silane according to general formula I, under conditions in which hydrolysis takes place, for example in the presence of water, of the radical $R^2$, is polycondensed or copolycondensed with at least one further hydrolysable silane compound.

In the simplest case, for example a previously described silane of general formula I can hereby be subjected to a polycondensing hydrolysis reaction. The hydrolysis can be implemented for example by the addition of water, however it can also be implemented by choice of suitable catalysts or under suitable conditions in the absence of water.

According to a further variant, also mixtures of different silanes of general formula I can be copolycondensed. Conceivable here is for example an embodiment in which the parameters a and b in the case of the silane of formula I are chosen to be different, for example silanes with a=1 and b=0 can be copolycondensed with silanes of formula I in which a=1 or 2 and b=0 or 1. By means of the previously mentioned modification, both the concentration of group P which can be made photolabile or is photolabile and also the reactivity, i.e. the readiness of the silane to hydrolyse, can be specifically adjusted.

According to a further embodiment, one or more of the previously mentioned silanes of formula I can be copolycondensed in addition with a further hydrolysable silane. For this purpose, for example alkoxy silanes can be used. These alkoxysilanes can be unmodified (i.e. for example carry no group P which can be made photolabile) or else carry further reactive radicals, for example radicals with unsaturated bonds, such as unsaturated double bonds, for example (meth)acrylic acid or (meth)acrylate groups. Due to the presence of further reactive organic radicals, crosslinking of the siloxane basic framework obtained by polycondensation is hence possible.

The previously mentioned hydrolysis reaction is preferably implemented in the presence of a catalyst, preferably ammonium fluoride.

By-products produced during the polycondensation, in particular compounds according to formula $R^2H$, are preferably separated from the reaction mixture during and/or after conclusion of the reaction, in particular by distilling off. In particular alcohols, such as for example methanol or ethanol (both produced corresponding to the choice of the radical $R^2$) can thus be separated from the reaction mixture easily and almost completely so that the equilibrium state of the polycondensation reaction is displaced towards the product side.

According to a further aspect, the present invention relates to method products of the previously presented polycondensation method, namely silicic acid (hetero)poly(co)condensates with positive-resist behaviour. Because of the possible crosslinkage during the (co)polycondensation, it is not possible to indicate a corresponding unequivocal structural formula for the obtained method products. However a siloxane network forms the basis of the silicic acid (hetero)poly(co)condensate. According to whether for example further reactive groupings are obtained in addition, a crosslinkage, for example by UV irradiation etc., can also be implemented in addition, an additional, second organic network being produced.

The silicic acid (hetero)poly(co)condensates (ORMOCERs) have a positive-resist behaviour in which during photoirradiation (in the case of a photolabile group) or with the addition of a corresponding reagent which forms a reactive species during photoirradiation and reacts with the group P which can be made photolabile, a chemical modification of the silicic acid (hetero)poly(co)condensate is effected. This can be for example the saponification of an ester grouping which is present (group which can be made photolabile) or the direct splitting of an azo grouping (photolabile group) which is contained for example. In this respect, the silicic acid (hetero)poly(co)condensates according to the present invention have a defined light sensitivity which leads to property changes.

ORMOCER®s already offer, as separate material class, a wide portfolio of application possibilities and adjustable properties which is determined in part by the photostructurability of the ORMOCER®s. The method of the negative-resist which is used exclusively at present thereby continually reaches its limits because of the organic solvents required in the development step. Frequently, photoresists are required on the user side, the solubility of which is provided in aqueous systems. The present invention offers a solution to this problem since the exposed regions of the system developed here are soluble in aqueous solutions (e.g. TMAH). In combination with the already very wide field of use of ORMOCER®s, new application possibilities therefore arise for the material class described in the present invention.

This property of the silicic acid (hetero)poly(co)condensates according to the present invention can be used in particular for photoresists. Therefore, a further aspect of the present invention relates to a photoresist with positive-resist behaviour, comprising a silicic acid (hetero)poly(co)condensate with positive-resist behaviour, as described previously, at least one solvent, preferably propylene glycol monomethylether-1,2-acetate (PGMEA, CAS-no.: 108-65-6), methyl isobutyl ketone, n-propyl acetate, butyl acetate, butyl lactate, ethanol or mixtures hereof, and also, in the case where a silicic acid (hetero)poly(co)condensate with a group P which can be made photolabile forms the basis of the photoresist, a photoactivatable compound which degrades the group P which can be made photolabile during photoactivation.

The photoresist can be applied for example on substrates, hardening is thereby effected for example by evaporation of the contained solvent. Consequently, a homogeneous and thin layer can be produced on any substrates.

The photoresists according to the invention can be used, for example either as so-called sacrificial resists or else as structurable functional layers.

If photoresists are used as photostructurable functional materials, the following applications inter alia are possible:
- structurable insulation materials as intermediate layer (interlayer dielectrics) or as final layer in/on electrical components. The photostructurability is used in order to enable through-/surface contacting. The material can then be modified such that it has low dielectric permittivity (<3.5).
- for capacitive use in thin-film capacitors, transistors etc. The material can be adjusted such that it has high dielectric permittivity (>3.5).
- passivation materials which protect electronic components against mechanical, electrical, electrostatic, chemical (from subsequent processes) stresses or environmental influences (moisture, oxygen . . . ).
- as protective or insulating material for applications in polymer electronics, flexible electronics or printable electronics.
- as template material in display technology or for other applications in which non-structurable, non-etchable materials (such as colourants) are intended to be applied, structured in the range <100 μm.
- for optical applications (microoptics, data transmission), the functional resist being able to be adjusted such that it has the required optical properties (refractive index, absorption, thermooptical coefficients . . . ). In the present invention, only long-term-stable applications with optical wavelengths >450 mm are conceivable.
- as material for structuring microfluidic structures, for example for lab-on-a-chip applications.

Preferred photoactivatable compounds are thereby in particular photoacid generators which are preferably configured from the group consisting of onium salt photoacid generators, halogen-containing photoacid generators, sulphonic acid- or sulphonate-containing photoacid generators.

Preferred acid generators which can also be used according to the present invention are mentioned for example in US 2005/007944 A1. All of the photoacid generators described there can also be used preferably according to the present invention.

Furthermore, it is possible to increase the resolution of the ORMOCER®-containing photoresist with positive-tone behaviour, presented here, by adding an additional additive which traps the reactive species which lead to the light-induced reaction and as a result prevents the reactive species from diffusing in large numbers into the non-exposed regions and likewise from being able to induce the formation of soluble components there. There are suitable for this purpose, for example amines as have also been reported in numerous other works relating to photoresists with positive-tone behaviour.

Furthermore, the resolution in photoresists which are based on positive-tone behaviour is generally better than in the corresponding negative-tone photoresists. Thus it can be expected that, in comparison with conventional ORMOCER®s, the resolution is improved and can in addition be increased even further by the contact exposure which is possible in this case.

Preferred acid generators which can also be used according to the present invention are for example mentioned in US 2005/007944 A1. All of the photoacid generators described there can also be used preferably according to the present invention.

In addition, the invention relates to a method for photochemical structuring of a previously presented photoresist in which a substrate is coated with the photoresist and the obtained layer made of the photoresist is exposed in regions with radiation,
 a) the photoactivatable compound being activated and consequently the group P which can be made photolabile is degraded, or
 b) the photolabile group P being degraded.

The irradiation of the photoresist in regions can be effected for example by corresponding partial shading of the substrate. For this purpose, methods known already from the state of the art can be used preferably, such as for example, UV lithography or multiphoton polymerisation.

After exposure, the substrate provided with the photoresist is preferably subjected to a development step, the coating being treated with an aqueous-alkaline solution, in particular an aqueous solution of tetramethylammonium hydroxide.

As a result of the treatment of the coating, i.e. of the photoresist layer, with an aqueous-alkaline solution, the regions at which degradation of the group P which can be made photolabile or of the photolabile group P has taken place are dissolved out of the polymer matrix or at least solvated. As a result, a structural change in the obtained photoresist layer takes place. The unmodified regions which have for example higher hydrophoby than the regions of the silicic acid (hetero)poly(co)condensate which are modified by the exposure thereby remain preserved as far as possible.

According to a further preferred embodiment, the coating is treated thermally after deposition and/or after exposure, preferably at temperatures of 60 to 200° C., further preferred of 100 to 140° C. and/or preferably over a period of 1 s to 10 min, further preferred of 30 s to 2 min.

The present invention is described in more detail with reference to the subsequent embodiments, given by way of example, and also the accompanying example and Figure without however restricting the invention to the illustrated preferred embodiments.

The invention describes the production and structuring of an inorganic-organic hybrid polymer based on ORMOCER®s (organically modified ceramics, filed trade mark of the Fraunhofer-Gesellschaft e. V.) and also the corresponding underlying monomers. This new hybrid polymer is distinguished by reacting, after deposition as layer, to a treatment with actinic radiation with increased solubility in aqueous solvents. As a result, the possibility is offered of structuring the initially uniformly applied polymer layer with actinic radiation by means of suitable methods (such as for example UV lithography or multiproton polymerisation). The increase in solubility based on interaction with light is termed positive-behaviour since the resulting structures are an image of the mask or exposure pattern which is used.

The photolytic degradation can be started by light-induced degradation of a catalyst and thus structurability of the material is made possible. As underlying reaction, the acid-catalysed hydrolysis of an ester, which is frequently used for photoresists with positive-behaviour, was chosen. The ester function thereby acts as protective group for a carboxylic acid function which, in comparison to the educt, has increased solubility in aqueous media and accordingly is also termed photolabile group. The ester group is thereby part of an ORMOCER®, i.e. an oligosiloxane which was produced in advance by hydrolysis- and condensation reactions. The basic framework of the ORMOCER® hence forms an organically modified, inorganic Si—O network. This can be modified furthermore also by the addition of further so-called crosslinkers.

The photostructured ORMOCER layer which is obtained therefrom can be used as so-called sacrificial resist for the subsequent structuring of layers situated under the ORMOCER or after an additional functional groups as photostructured, functional coating.

The organic substituents of the alkoxysilanes forming the basis of the ORMOCER®s if they have corresponding functional groups can enable light-induced polymerisability of the ORMOCER®. To date, only ORMOCER®s with negative-tone behaviour have been developed in this way, e.g. by means of polymerisable methacrylate-, styryl-, epoxide- or norbornene-containing groups. In contrast to the above-mentioned two-component systems or (block)copolymers, the distribution of the silicon ions in the ORMOCER®s according to the invention is very homogeneous, for which reason this material class is very well suited as base for the development of novel positive-resists.

The photolabile group is thereby integrated by means of a thiol-ene reaction into the alkoxysilane forming the basis of the ORMOCER®. Subsequently, the formation of the SiO network is effected by hydrolysis- and condensation reactions with suitable catalysts. Typical catalysts for these reactions are acids or bases. The requirement thereby resides in maintaining the acid-labile group, which can also be split off under strongly alkaline conditions, in the alkoxysilane and not being split off once again. Within the scope of the present invention, this is effected under ammonium fluoride catalysis. In the case of photochemical structuring of negative-tone ORMOCER®s by means of UV lithography, a spaced exposure is thereby absolutely necessary since, even after the temperature treatment in the pre-bake step of the ORMOCER® film, it is still not solid and the mask can be damaged or greatly contaminated by contact exposure.

EMBODIMENTS

Example 1

Synthesis of the Monomer

Monomer production of an ORMOCER® with photolabile substituents

In a flask rinsed with argon, 55.45 mmol (7.886 g) of t-butyl methacrylate is introduced and diluted with 16.99 g of n-propyl acetate. Subsequently, 55.45 mmol (13.222 g) of 3-mercaptopropyl triethoxysilane is added thereto. A newly produced 88% KOH solution (3.13 g, 0.55 mmol KOH) is added slowly to the mixture in drops.

Conversion of the silane according to the invention is thereby effected by thiol-ene reaction of the thiol group to the unsaturated grouping of the acrylate group.

Example 2

Production of the Polycondensate

After conclusion of the reaction in example 1, there is added to a fifth of the batch, 101 µl of a 1.1 M $NH_4F$ solution and also 16.6 mmol (0.299 g) of water and the reaction mixture is agitated for 16 h at 25° C. Subsequently, 22.8 ml of PGMEA is added to the reaction mixture and the synthesis product is obtained by distillative removal of the volatile components released during the hydrolysis and condensation. The solvent PGMEA is thereby left in the reaction mixture so that already a finished photoresist is obtainable.

Example 3

Structuring and Development of the Photoresist

The synthesis product which already comprises the solvent PGMEA is applied on a substrate, after addition of a photoacid generator (PAG, Cyracure 6975), by means of centrifugal coating. With the dilution, the thickness of the photoresist can be adjusted, for example to 500-1,000 nm. After the centrifugal deposition, a pre-bake is implemented for 1 min at 120° C. Subsequently, the layer is exposed in a mask exposer (Hg vapour lamp, I-line) for 30 s. In the next step, a post-exposure bake is effected for a further 1 min at 120° C. The exposed places can be developed subsequently with an aqueous-alkaline solution (TMAH). The non-exposed product can likewise be removed (stripping), in the subsequent process for example by means of methylisobutyl ketone.

Example 4

Etching Stability

The layer obtained after the photostructuring and development was subsequently subjected to an argon plasma (power: 300 W, argon pressure: 1.0*10.3 mbar). The plot of the time-dependent removal shows that the ORMOCER® underlying this invention behaves with positive-tone behaviour, relative to a back-sputtering process (argon plasma), in at least as stable a manner as conventionally crosslinked ORMOCER®s (FIG. 1).

ORMOCER®s already offer, as separate material class, a wide portfolio of application possibilities and adjustable properties which is determined in part by the photostructurability of the ORMOCER®s. The method of the negative-resist which is used exclusively at present thereby reaches its limits time after time because of the organic solvents required in the development step. Frequently, photoresists, the solubility of which is provided in aqueous systems, are demanded on the part of the user. The present invention offers a solution to this problem since the exposed regions of the system developed here are soluble in aqueous solutions (e.g. TMAH). In combination with the already very wide application field of the ORMOCER®s, new application possibilities arise therefore for the material class described in the present invention.

Furthermore, the resolution in photoresists which are based upon positive-tone behaviour is generally better than in the corresponding negative-tone photoresists. Thus, it can be expected that, in comparison to conventional ORMOCER®s, the resolution is improved and can be increased even further in addition by means of the contact exposure which is possible in this case.

The invention claimed is:
1. A photoresist with positive-resist behaviour, consisting of
   a) a silicic acid (hetero)poly(co)condensate with positive-resist behaviour, which is producible from a silane of general formula I

$$[P-(Y^1)_c-X-(Y^2)_c]_a Si(R^1)_b (R^2)_{4-a-b}$$   Formula I

P being a group which can be made photolabile and being selected from the group consisting of radicals of general formula IV,

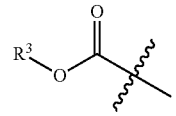

Formula IV $R^3$ being selected from the group consisting of linear or branched alkyl radicals with 1 to 18 carbon atoms, trialkylsilyl groups, and ester groups,
   X representing the grouping:

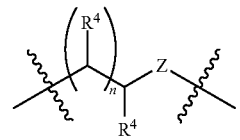

Z being selected from the group consisting of S, O, $NR^4$, and $C(R^4)_2$,
   $R^4$ being the same or different with each occurrence and being selected from the group consisting of hydrogen and linear or branched alkyl radicals with 1 to 18 carbon atoms, cycloaliphatic groups with 6 to 24 carbon atoms or aromatic groups with 6 to 24 carbon atoms and
   n being 1,
   $Y^1$ and $Y^2$ being the same or different with each occurrence and being selected from the group consisting of saturated or unsaturated alkylene groups with 1 to 18 carbon atoms, cycloaliphatic groups with 6 to 24 carbon atoms and aromatic groups with 6 to 24 carbon atoms,
   $R^1$ being selected from the group consisting of linear or branched alkyl radicals with 1 to 18 carbon atoms, cycloaliphatic groups with 6 to 24 carbon atoms and aromatic groups with 6 to 24 carbon atoms, $R^2$ representing an —$OR^3$ group, $R^3$ being selected from the group consisting of linear or branched alkyl radicals with 1 to 18 carbon atoms, cycloaliphatic groups with 6 to 24 carbon atoms and aromatic groups with 6 to 24 carbon atoms, a being 1, 2 or 3, b being 0, 1 or 2, with the condition that a and b are chosen such that there applies: 4-a-b≥1, c being 0 for the radical $Y^1$ and 1 for the radical $Y^2$, in which the silane of general formula I under conditions in which hydrolysis takes place, of the radical $R^2$, is polycondensed or copolycondensed with at least one further hydrolysable silane compound, b) at least one solvent, and c) a photoactivatable compound which during photoactivation degrades the group P which can be made photolabile.

2. The photoresist according to claim 1, wherein the at least one solvent is selected from the group consisting of propylene glycol monomethylether-1,2-acetate (PGMEA, CAS-no.: 108-65-6), methyl isobutyl ketone, n-propyl acetate, butyl acetate, butyl lactate, ethanol or mixtures thereof.

3. The photoresist according to claim 1, wherein the photoactivatable compound is a photoacid generator which is selected from the group consisting of onium salt photoacid generators, halogen-containing photoacid generators, and sulphonic acid- and sulphonate-containing photoacid generators.

4. A method for photochemical structuring of a photoresist according to claim 1, wherein a substrate is coated with the photoresist by centrifugal coating and the obtained layer made of the photoresist is exposed in regions with radiation, wherein a) the photoactivatable compound being activated and consequently the group P which can be made photolabile being degraded, or b) the photolabile group P being degraded.

5. The method according to claim 4, wherein the photoresist, after exposure, is subjected to a development step, the coating being treated with an aqueous-alkaline solution.

6. The method according to claim 4, wherein the coating is treated thermally after deposition and/or after exposure.

7. The method according to claim 6, wherein the coating is treated thermally at temperatures of 60 to 200° C. over a period of 1 s to 10 min, after deposition and/or after exposure.

8. The photoresist according to claim 1, wherein $R^3$ is selected from the group consisting of t-butyl-, 1-ethylnorbornyl-, 1-methylcyclohexyl-,1-ethylcyclopentyl-, 2(2-ethyl)adamantyl-, t-amyl, trimethylsilyl-, triethylsilyl-dimethyl-tert-butylsilyl, and t-butoxycarbonyloxy (t-BOC), and 3-oxocyclohexyl group.

9. The photoresist according to claim 8, wherein the photoactivatable compound is a photoacid generator which is selected from the group consisting of onium salt photoacid generators, halogen-containing photoacid generators, and sulphonic acid- or sulphonate-containing photoacid generators.

10. A method for photochemical structuring of a photoresist according to claim 8, wherein a substrate is coated with the photoresist and the obtained layer made of the photoresist is exposed in regions with radiation, a) the photoactivatable compound being activated and consequently the group P which can be made photolabile being degraded, or b) the photolabile group P being degraded.

11. The method according to claim 10, wherein the photoresist, after exposure, is subjected to a development step, the coating being treated with an aqueous-alkaline solution.

* * * * *